United States Patent [19]

Collins et al.

[11] Patent Number: 4,988,293
[45] Date of Patent: Jan. 29, 1991

[54] TOUGHNESS COATING FOR CRYSTALLINE ORTHODONTIC BRACKETS

[75] Inventors: Paul R. Collins, Washougal, Wash.; Larry R. Rothrock, Poway, Calif.

[73] Assignee: Union Carbide Chemicals and Plastics Company Inc., Danbury, Conn.

[21] Appl. No.: 268,186

[22] Filed: Nov. 7, 1988

[51] Int. Cl.⁵ .............................................. A61C 7/00
[52] U.S. Cl. ............................................ 433/8; 433/9
[58] Field of Search ........................................ 433/8, 9

[56] References Cited

U.S. PATENT DOCUMENTS

| 3,504,438 | 4/1970 | Wittman et al. | 433/8 |
| 4,050,156 | 9/1977 | Chasanoff et al. | 433/8 |
| 4,302,532 | 11/1981 | Wallshein | 433/8 |
| 4,595,598 | 6/1986 | De Luca et al. | 433/9 |
| 4,820,545 | 4/1989 | Negrych | 433/217.1 |

Primary Examiner—Gene Mancene
Assistant Examiner—Michael Lynch
Attorney, Agent, or Firm—Morris N. Reinisch

[57] ABSTRACT

A single crystal orthodontic bracket is disclosed which is provided with an outer protective layer of a polycrystalline material so as to provide fracture toughness of the orthodontic bracket.

11 Claims, 1 Drawing Sheet

TOUGHNESS COATING FOR CRYSTALLINE ORTHODONTIC BRACKETS

BACKGROUND OF THE INVENTION

1. Field Of The Invention

This invention pertains to the field of orthodontic brackets. More particularly, the present invention is directed to orthodontic brackets being composed of single crystal oxides, such as, a crystalline alpha alumina, zirconia, yttria, magnesia, titania, strontium titanate, and the like, wherein at least a portion of the bracket is provided with an outer protective coating layer of a polycrystalline oxide material. The polycrystalline outer layer improves the fracture toughness of the orthodontic bracket.

2. Discussion Of Related Art

Orthodontic brackets attach directly to teeth and serve to transmit corrective forces from an orthodontic arch wire to the tooth to which the bracket is attached. The requirements for an orthodontic bracket are quite severe. Firstly, it must have sufficient mechanical strength to withstand the forces to which it will be subjected, including the forces transmitted by an arch wire, ligation forces, and mastication forces. Secondly, it must be chemically inert in the oral environment so that it will not corrode and will be and remain biologically inert. The bracket must meet these requirements, and still remain small enough to fit on the tooth.

The overwhelming majority of orthodontic brackets in use today are made of metal, usually stainless steel. Metal brackets meet all of the essential requirements, but they have one undesirable attribute—they are unsightly. A person undergoing orthodontic treatment has a conspicuous amount of metal in full view on the front surfaces of his or her teeth. Since the treatment extends over a number of years, this unsightly appearance must be endured for a considerable period of time.

The incentive to make brackets from less unsightly materials has existed for many years. But recently, orthodontic treatment has been given to increasing numbers of adults, for whom the unsightly appearance of metal brackets is more than a mere annoyance. Ceramic brackets have been proposed but have a tendency to stain, especially if the bracket must be worn for extended periods of time. Consequently, the incentive to provide more esthetic orthodontic treatment is even greater now than it has ever been.

Recently, sapphire (crystalline alpha-alumina) has found commercial application as the material of construction for orthodontic brackets. U.S. Pat. No. 4,639,218 discloses sapphire orthodontic brackets, and sapphire orthodontic brackets are currently manufactured and sold by "A" Company, Inc., a subsidiary of the Johnson & Johnson Company, and Ormco Corporation. While these brackets are esthetically pleasing, i.e., are transparent and do not stain, concerns still exist about the durability of these brackets made from sapphire under the considerable stresses on the bracket induced by the arch wire, ligation and mastication.

Thus, sapphire is more subject to fracturing and chipping than metal. Quite commonly, such fracturing and chipping are initiated by surface damage caused during arch wire installation or by mishandling prior to installation. Due to the small size of these brackets, typically about 1 to 5 millimeters, even a shallow surface defect can be enough to cause a fracture along a crystal lattice in the bracket under the sizable stress of the arch wire. This susceptibility of the crystalline material to fracturing and chipping is clearly undesirable from the standpoint of its use as an orthodontic bracket.

Accordingly, it is desired to provide crystalline orthodontic brackets having enhanced resistance to fracturing and chipping during both installation and use.

SUMMARY OF THE INVENTION

By this invention, crystalline orthodontic brackets are provided that exhibit enhanced resistance to fracturing and chipping during installation and use. Moreover, the orthodontic brackets of this invention exhibit desirable transparency and resistance to staining and are chemically inert.

The orthodontic brackets of the present invention comprise a body having a base face (the side intended to face the tooth); a front face on the side opposing the base face, the front face defining a longitudinal arch wire groove; upper and lower sides extending between the base face and front face and edge faces between which faces the arch wire groove extends.

In accordance with the present invention, at least a portion of such a crystalline orthodontic bracket, advantageously the groove in which the arch wire is placed, is provided with a protective outer layer of a polycrystalline material, preferably a polycrystalline oxide material. This polycrystalline coating layer may be comprised of the same material from which the single crystal orthodontic bracket is comprised or, alternatively, may be comprised of an entirely different material.

Thus, the polycrystalline coating layer may, for example, be comprised of alpha-alumina, zirconia, yttria, magnesia, titania, strontium titanate, other rare earth oxides and the like, or a combination thereof. Alternatively, the polycrystalline material may also be comprised of $SiO_2$ (glass), or thin metallic films (e.g., silicon, aluminum, etc.). These alternative materials would be thin enough so that they would allow light to pass through and therefore not be unsightly.

The polycrystalline coating layer provides a number of distinct advantages. Firstly, the susceptibility of the polycrystalline to fracture initiation by surface damage or stress is generally less than that for the single crystalline material, particularly when the single crystalline material is comprised of sapphire. Accordingly, the polycrystalline material provides a tough protective outer layer. Secondly, and perhaps even more importantly, even if the polycrystalline coating layer does fracture, the fracture will generally proceed no further than the interface formed between the polycrystalline material and the single crystalline material of which the base structure of the orthodontic bracket is made. Thus, the poly/single crystalline interface effectively prevents further propagation of the fracture into the single crystalline material itself. In effect, the polycrystalline coating layer acts in a sacrificial manner to prevent bracket failure.

Accordingly, the present invention comprises an orthodontic bracket comprising a single crystal oxide having at least a portion of the bracket provided with an outer coating layer of polycrystalline material.

Hence, as a result of the present invention, crystalline orthodontic brackets are provided which exhibit excellent resistance to fracturing and chipping during its installation and its functioning within the mouth of the user.

DETAILED DESCRIPTION OF THE INVENTION

Figure 1:
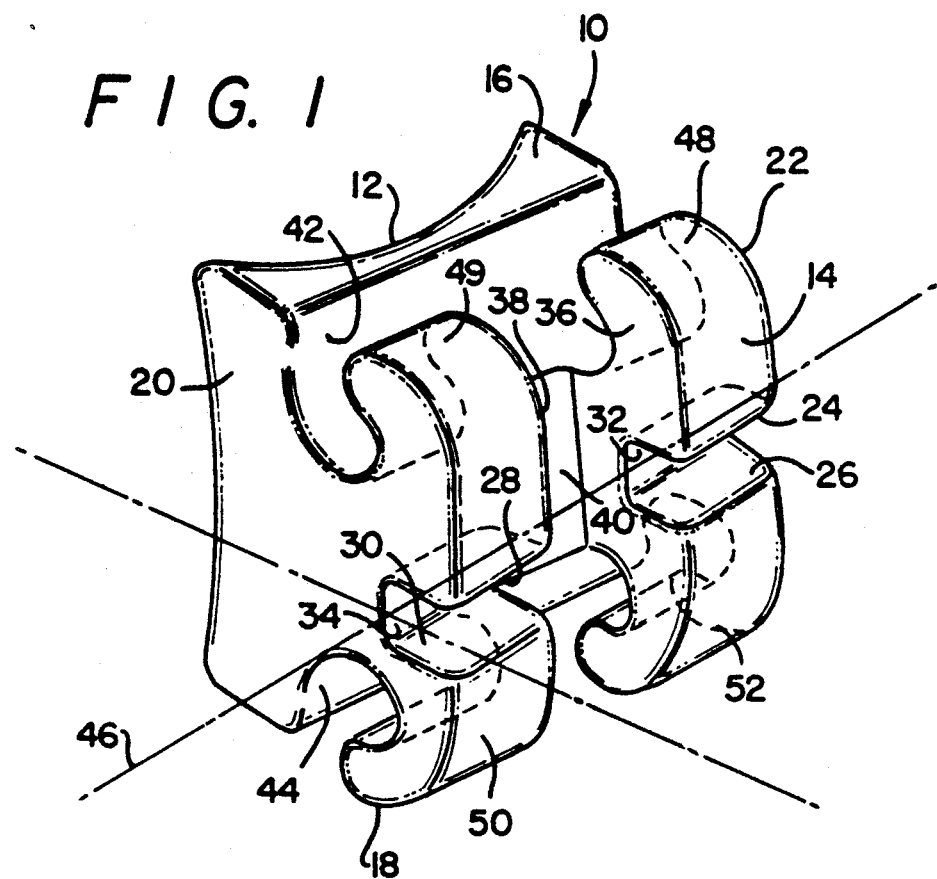
FIG. 1 is a perspective view of an orthodontic bracket made of crystalline alpha-alumina.

As used herein, the term "crystalline material" is intended to include only essentially monocrystalline material, that is, material comprised of a single crystal or two or more single crystals grown together longitudinally but separated by a relatively small angle (usually within 4°, determined with respect to the axes of neighboring single crystals) grain boundary. Most preferably, these grain boundaries do not vary by more than about 1°.

The crystalline material may solely consist of the material, i.e., zirconium and oxygen atoms in the case of zirconia, or may contain minor amounts of impurities or dopants, i.e., metal elements which become incorporated into the crystalline framework.

Also as used herein, the term "polycrystalline" as the term implies, is intended to include a material comprised of a multitude of small, randomly oriented crystalline grains. The grain size will depend on the material and the method of preparation, but is generally less than 100,000 Angstroms. Certain amorphous glasses (e.g., $SiO_2$) may also be a suitable coating and should not be construed to be excluded by the term "polycrystalline".

Crystalline stock can be produced by various techniques from the molten material. One technique is the EFG (for Edge defined, Film fed, Growth) technique which is a modification of the Czochralski process for growing crystalline materials. An EFG process is the process described in U.S. Pat. No. 4,639,218 for making a crystalline alpha-alumina rod having a cross-sectional configuration approximating that of an orthodontic bracket. The EFG process is described by LaBelle in "EFG - The Invention and Application to Sapphire Growth", in Journal of Crystal Growth, 50, pages 8–17 (September, 1980). See also LaBelle, U.S. Pat. No. 3,591,348; LaBelle, et al, U.S. Pat. Nos. 3,701,636 and 3,915,662, and other patents and articles cited in the Journal of Crystal Growth article. Similar techniques can be utilized to grow the crystalline materials for use in the orthodontic brackets of this invention.

Another technique is the Czochralski process in which a single crystal boule of the crystalline material is drawn from a melt. The boules may be sliced to provide flat stock material for fabrication.

Although the EFG technique can provide the advantage of a near net cross-sectional shape, the Czochralski technique is typically preferred to provide crystalline stock material for orthodontic brackets. There are several reasons for this preference. The Czochralski technique does not involve the use of any dies as does the EFG technique. The dies, which operate at the high temperatures of the melt, can be a source of contaminants to the crystalline stock. These contaminants can adversely affect the light transmission and/or color quality of the crystalline material. Also, the EFG technique is prone to inducing more strain within the crystal structure. Another problem which usually occurs in greater frequency with the EFG technique than the Czochralski technique is the inclusion of defects within the crystal structure such as bubbles. Moreover, the bar stock from the EFG technique generally has exterior ridges or waves caused by the interaction of the die and the melt, the surface of which freezes as it passes through the die.

With reference to FIG. 1, an orthodontic bracket 10 having two pair of tie wings is fabricated completely of crystalline material. The bracket has base face 12 which is depicted as being concave to fit the curvature of the tooth. Front face 14 is that face seen when directly looking at the mouth of the patient. Front face 14 may be parallel to the plane generally defined by the base face; however, the front face and the base face are typically at an angle of up to about 15° with respect to each other to facilitate the function of the orthodontic bracket. The bracket also defines top side 16 and bottom side 18 and edges 20 and 22. As can readily be seen from the Figure, the faces and sides can be curved. For the sake of the ease of understanding, the top and bottom faces, sides and edge faces referred to herein may be described as being in a plane. The plane referenced is that most closely characteristic of the orientation of the face, side or edge to which reference is being made.

The dimensions of the bracket may vary. Usually, the width (average distance between the faces) is between about 1 and 5 millimeters, the height (average distance between the planes of the top and bottom sides) is between about 1 and 5 millimeters, and the thickness (average distance between the planes of the front and back faces) is between about 1 and 4 millimeters. The dimensions are selected from functional and esthetic standpoints.

Figure 2:
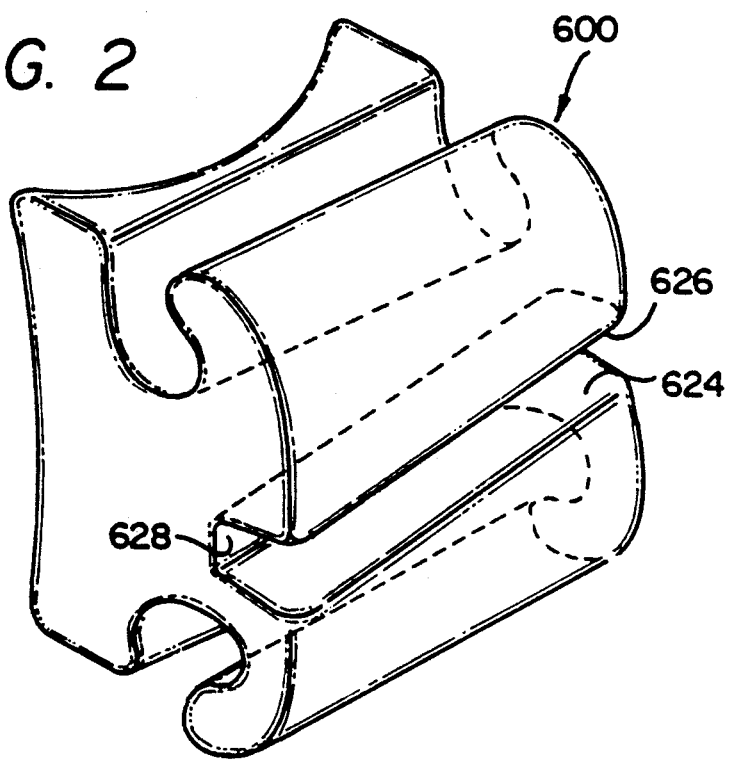
FIG. 2 is a perspective view of a "single-winged" orthodontic bracket.

The front face defines an arch wire groove which extends between edge faces 20 and 22. The arch wire groove is defined by walls 24, 26, 28, 30, 32, and 34, and the "saddle" is defined by walls 36, 38, 40 of a double tie wing, or twin bracket (such as is shown in FIG. 1 . A single wing bracket 600 is shown in FIG. 2. In the single wing bracket 600, the arch wire groove is defined by wall 624, 626, and 628, and no saddle exists. The arch wire groove may extend normal to the axis of an edge face or at an angle thereto, e.g., up to about 20°, for purposes of enhancing the function of the orthodontic bracket. The edge faces are depicted as being at right angles to the top and bottom sides; however, the edge faces and sides may form a structure having a trapazoidal cross-sectional configuration, e.g., a parallelogrammic or rhombohedric cross-section, in which case, the arch wire groove is often substantially parallel to the planes defined by the top and bottom surfaces. See, for example, U.S. Pat. No 4,415,330.

The arch wire groove is sized to receive the arch wire extending between the teeth. Accordingly, the groove is relatively small, often about 0.4 to 0.6 (typically about 0.5) millimeter in depth. The bottom surface 34 of the arch wire groove is normally flat due to machinery considerations although curved configurations may also be used. The bottom surface 28 and 34 of the arch wire groove can be equidistant from the front surface or may be closer to the front face at certain regions than others. The particular design will depend upon the designer and the functions sought after. For the purposes of the description herein, the longitudinal axis 46 of the arch wire groove shall be the axis most closely characterized by the arch wire groove.

The top and bottom sides have surfaces 42 and 44, respectively, which define the tie wing sections 48, 49, 50 and 52 of the orthodontic bracket. As depicted in FIG. 1, surfaces 42 and 44 are indentations in the top and bottom sides. Alternatively, the tie wings may extend outwardly from the top and bottom surface. The tie wings are most often the portions of the orthodontic bracket to break during fabrication as well as during installation use. The breaks may involve a fracture between the bottom surface of the tie wing groove and the indentation defined by either surface 42 or 44, or alternatively may involve chipping of the tips of the tie wings.

The machining of the orthodontic brackets may be effected by any suitable technique. Often, blanks are prepared and then by a series of cutting, grinding, polishing steps, the bracket is fabricated. A diamond cutting wheel can be used to cut out the arched wire groove. Edges may be bevelled by grinding, and corners rounded off by polishing. Subsequent annealing treatments can also be used. The brackets are preferably polished after annealing to smooth off contours and to remove any surface imperfections which could encourage propagation or fractures. A flux polishing procedure can be used.

By this invention, a toughness coating is provided for at least the arch wire groove of the orthodontic bracket defined by walls 24, 26, 28, 30, 32 and 34 as depicted in FIG. 1 and walls 24, 26 and 28 as shown in FIG. 2. Of course, if desired, the entire bracket may be coated with the toughness coating of the present invention.

The orthodontic bracket is made from transparent, crystalline oxide material such as, for example, alpha alumina (sapphire), zirconia, yttria, magnesia, titania, strontium titanate, and other rare earth oxide crystalline materials. The coating layer of the present invention is a polycrystalline oxide material and may comprise the polycrystalline form of the crystalline material used for making the basic orthodontic bracket structure or may comprise a combination of such materials. A preferred polycrystalline material is $Al_2O_x$ (where $x=2-3$).

The coating layer may be provided on the orthodontic bracket in any conventional manner known to those skilled in the art. For example an $Al_2O_x$ ($x=2-3$) coating can be formed on the surface of the orthodontic bracket by the evaporation of molten alumina in a vacuum. More particularly, utilizing an electron beam to vaporize a small (typically 1-5 mm) area of an alumina sample in vacuum, the $Al_2O_x$ will travel in line-of-sight trajectory to the bracket. Generally, the bracket will be held about 6 inches to almost 24 inches from the vaporizing alumina to provide uniform coverage. By suitable masking of the bracket, selected areas of the bracket can be coated (e.g., the arch wire groove).

The alumina may be heated to the evaporation point by any other method which is well known to those skilled in the art. Typically, the alumina may be heated by electron beam heating, RF (radio frequency) induction heating, laser heating, or the like. The required polycrystalline layer is formed by condensation of the evaporated alumina onto the desired surfaces of the orthodontic bracket. Generally, control of the rate of evaporation is important in order to provide good adhesion of the polycrystalline film layer to the orthodontic bracket. This rate is easily determinable by one skilled in the art and should be fast enough to be economically and commercially acceptable but still be slow enough to provide the necessary adhesion of the polycrystalline layer to the substrate.

Moreover, the temperature of the orthodontic bracket may also be controlled for improved adhesion. In particular, the temperature of the orthodontic bracket may be regulated by infrared lamps within the chamber to achieve temperatures of up to 300° C. Generally the higher the temperature, the better the adhesion, but 300° C. is adequate for most materials.

Yet an alternative method for forming a polycrystalline film such as $Al_2O_x$ onto the orthodontic bracket is by vacuum deposition of aluminum metal with subsequent thermal oxidation of the aluminum film to form the $Al_2O_x$ polycrystalline material.

As in the previous method of forming the polycrystalline layer, the conditions for aluminum deposition, such as the rate of evaporation and subsequent deposition as well as the temperature of the orthodontic bracket are important control parameters for providing proper adhesion of the polycrystalline coating layer onto the orthodontic bracket. Moreover, in this alternative embodiment, the oxidation conditions, namely, the temperature and oxygen concentration for oxidizing the alumina film, are result effective variables in producing the desired $Al_2O_x$ film. The temperature and oxygen concentration conditions in order to promote the formation of $Al_2O_x$ would be well within the knowledge of those skilled in the art.

Generally, the thickness of the coating layer that is applied to the orthodontic bracket for providing fracturing and chipping resistance is typically about 1,000 to 50,000 Angstroms and, preferably, up to about 10,000 Angstroms. Obviously, for a material which is not inherently transparent, the thickness of the coating layer will be desirably be less, generally up to about 2,000 Angstroms.

In alternative embodiments of the present invention, the most critical load bearing portions of the bracket are made of a crystalline material, while the remainder may be made of yet another transparent material such as polycarbonate or polysulfone plastic, which are both less expensive, easier to work with, and easier to bond to the tooth. In such alternative embodiments, obviously only the crystalline material of the orthodontic bracket would be treated in accordance with the present invention so as to provide the polycrystalline oxide outer layer.

Bonding a crystalline orthodontic bracket to the tooth (or to a plastic base or to any other substrate) must be done with care. Many of the ordinary orthodontic cements (which are usually acrylic resins) will not adhere well to crystalline material without taking steps to enhance the adhesion. One means of enhancing the adhesion of the crystalline bracket to the tooth is illustrated in FIGS. 13 and 14 of U.S. Pat. No. 4,639,218 in which a bracket is shown having an undercut or keyway in the back face of the bracket. Orthodontic cement filling the keyway will have enhanced mechanical adhesion to the bracket because of the undercut portion. The undercuts can also serve as slots for the insertion of pliers or the like for the orthodontic treatment.

Another means of enhancing the adhesion cements such as acrylic resins to a crystalline bracket is to alter the surface of the crystalline material in such a way as to increase to strength of the adhesive bond between the crystalline material and the cement. It is known, for instance, that a wide variety of silicone coupling agents can be used to enhance the adhesive force between siliceous substrates and a wide variety of thermosetting plastics. This technology may be utilized by coating the crystalline surface that is to be in contact with the cement with a thin coating (usually thinner than about 10,000 Angstroms, and preferably, up to about 1,000

Angstroms) of a siliceous material such as silica, and using silicone or silane coupling agents to enhance the bond of that surface to the cement, in a manner analogous to that which is presently known. Examples of means for coating the crystalline siliceous material are cathode sputtering, plasma deposition, and electron beam evaporation, all of which are known techniques, especially in the semiconductor arts.

The crystalline bracket having its base or tooth contacting surface sputter coated with silica or other siliceous material such as a glass, has excellent affinity for silicone coupling agents such as A-174 (gamma-methacryloxypropyltrimethoxysilane), and by using such coupling agent the adhesion of the bracket to acrylic orthodontic cement is enhanced.

Another method for enhancing the affinity of the crystalline bracket to silicone coupling agents is heat the brackets to remove adsorbed water, and then treat the bracket with a dilute solution (e.g., 2 to 2.5 weight percent solution in toluene/propolyene glycol monomethyl ether) of a silane coupling agent such as A-174.

A particularly useful test for evaluating orthodontic brackets is to insert a flat blade into the arched wire groove and twist the blade around an axis perpendicular to the longitudinal axis of the arch wire groove. The greater the force required to fracture the bracket, the better the crystal orientation within the bracket.

The orthodontic bracket of the present invention not only has enhanced esthetics because of the transparency of the crystalline material, but most importantly, provide an outer toughness, fracture-resistant coating to the bracket which acts as a sacrificial layer and helps prevent fracturing and chipping of the bracket.

What is claimed is:

1. An orthodontic bracket comprising a body comprising a single crystalline oxide material having a base face intended to face a tooth and an opposing front face defining a longitudinal arch wire groove, and having a polycrystalline outer coating layer on at least a portion of the bracket, said polycrystalline outer coating layer being a material selected from the group consisting of alpha-alumina, zirconia, yttria, magnesia, titania, strontium titanate, rare earth oxides, $Al_2O_x$ (x=2-3), and combinations thereof.

2. The orthodontic bracket of claim 1, wherein the single crystal oxide material is selected from the group consisting of alpha-alumina, zirconia, yttria, magnesia, titania and strontium titanate.

3. The orthodontic bracket of claim 1, wherein the single crystal oxide bracket material is made entirely of crystalline alpha-alumina.

4. The orthodontic bracket of claim 3, wherein the crystalline alpha-alumina is sapphire.

5. The orthodontic bracket of claim 1, wherein the single crystal oxide bracket material is made entirely of zirconia.

6. The orthodontic bracket of claim 1, wherein the single crystalline oxide bracket material is made entirely of yttria.

7. The orthodontic bracket of claim 1, wherein the thickness of the polycrystalline outer coating layer is in the range of from about 1,000 to 50,000 Angstroms.

8. The orthodontic bracket of claim 1, wherein the polycrystalline outer coating layer coats the arch wire groove.

9. The orthodontic bracket of claim 1, wherein the polycrystalline outer coating layer coats the entire bracket.

10. The orthodontic bracket of claim 1, wherein the arch wire groove is oriented essentially parallel to the top and bottom faces of the bracket.

11. The orthodontic bracket of claim 1, wherein the bracket has a rhomboidal configuration when viewed looking directly at the front of the bracket.

* * * * *